(12) United States Patent
Klee et al.

(10) Patent No.: US 12,303,574 B2
(45) Date of Patent: May 20, 2025

(54) DENTAL COMPOSITION

(71) Applicants: DENTSPLY SIRONA INC., York, PA (US); DENTSPLY DETRELY GMBH, Constance (DE)

(72) Inventors: Joachim E. Klee, Radolfzell (DE); Florian Szillat, Neukirchen-Vlyun (DE); Julie Kirschner, Dambach-la-Ville (FR); Jacques Lalevee, Mulhouse (FR)

(73) Assignee: Dentslpy Sirona Inc., York, PA (US)

( * ) Notice: Subject to any disclaimer, the term of this patent is extended or adjusted under 35 U.S.C. 154(b) by 587 days.

(21) Appl. No.: 17/638,474

(22) PCT Filed: Aug. 28, 2020

(86) PCT No.: PCT/EP2020/025386
§ 371 (c)(1),
(2) Date: Feb. 25, 2022

(87) PCT Pub. No.: WO2021/037396
PCT Pub. Date: Mar. 4, 2021

(65) Prior Publication Data
US 2023/0000727 A1     Jan. 5, 2023

(30) Foreign Application Priority Data
Aug. 30, 2019  (EP) .................................. 19194736

(51) Int. Cl.
| | |
|---|---|
| *C08F 2/46* | (2006.01) |
| *A61K 6/62* | (2020.01) |
| *A61K 6/889* | (2020.01) |
| *C08F 2/50* | (2006.01) |
| *C08G 61/04* | (2006.01) |

(52) U.S. Cl.
CPC ............. *A61K 6/62* (2020.01); *A61K 6/889* (2020.01)

(58) Field of Classification Search
CPC . A61K 6/889; A61K 6/62; A61K 6/60; A61K 6/887; A61K 6/54; A61K 6/30; C08L 33/10
USPC ...... 522/16, 12, 7, 6, 189, 184, 71, 1; 520/1
See application file for complete search history.

(56) References Cited

U.S. PATENT DOCUMENTS 4,411,625 A * 10/1983 Koblitz .................. A61K 6/887
                                                          433/199.1

FOREIGN PATENT DOCUMENTS

| | | |
|---|---|---|
| EP | 3785692 A1 | 3/2021 |
| JP | 09002915 A | 1/1997 |
| JP | 2009541375 A | 11/2009 |
| JP | 2013538837 A | 10/2013 |
| JP | 2017141213 A | 8/2017 |
| JP | 2019518731 A | 7/2019 |
| JP | 2019030517 A | 8/2019 |
| WO | WO-2017060527 A1 * | 4/2017 ........... A61K 6/0017 |
| WO | WO-2021037396 A1 | 3/2021 |

OTHER PUBLICATIONS

Shi et al, Influence of chemical structures of benzodioxole-based coinitiators on the properties of the infilled dental resin, 2010, Acta Biomaterialia, 6, 3067-3071 (Year: 2010).*
Japanese Office Action dated Jul. 9, 2024.
Makoto Oguri et al.; "Effects of functional monomers and photo-initiator on the degree of conversion of a dental adhesive"; Acta Biomaterialia; 2012, 8; 1928-1934; (DOI: 10.1616/j.actbio.2012.01.013).
International Preliminary Report on Patentability; PCT/EP2020/025386; Nov. 13, 2020 (completed); Jan. 19, 2021 (mailed).
Chinese Office Action dates Apr. 26, 2024.
Suqing Shi et al.; "A natural component as coinitiator for unfilled dental resin composites"; Journal of Biomedical Materials Research. Part B: Applied Biomaterials; vol. 82B, No. 1; Jun. 6, 2007; pp. 44-50.
Klocke Arndt et al.; "Plasma arc curing lights for orthodontic bonding"; American Journal of Orthodontics and Dentofacial Orthopedics; vol. 122, No. 6; Jan. 1, 2002; pp. 643-648.
Shi S. et al.; "Influence of chemical structures of benzodioxole-based coinitiators on the properties of the unfilled dental resin"; Acta Biomaterialia, Elsevier, Amsterdam, NL; vol. 6, No. 8; Aug. 1, 2010; pp. 3067-3071.
"European Application Serial No. 19194736.5, Extended European Search Report mailed Jul. 1, 2020", 16 pgs.
"European Application Serial No. 19194736.5, Partial European Search Report mailed Jan. 8, 2020", 20 pgs.
"International Application Serial No. PCT/EP2020/025386, International Search Report mailed Jan. 19, 2021", 7 pgs.
"International Application Serial No. PCT/EP2020/025386, Written Opinion mailed Jan. 19, 2021", 13 pgs.

* cited by examiner

*Primary Examiner* — Jessica Whiteley
(74) *Attorney, Agent, or Firm* — SCHWEGMAN LUNDERG & WOESSNER, P.A.

(57) ABSTRACT

The present invention is related to a dental composition comprising at least one polymerizable monomer having at least one ethylenically unsaturated group; and a radical initiator system comprising a photosensitizer having an absorption maximum ranging from 400 nm to 800 nm; and at least one CH-acidic compound as coinitiator.

19 Claims, 4 Drawing Sheets

DENTAL COMPOSITION

FIELD OF THE INVENTION

The present invention relates to a dental composition comprising at least one polymerizable monomer having at least one ethylenically unsaturated group and a radical initiator system, which comprises a photosensitizer having an absorption maximum ranging from 400 nm to 800 nm and at least one CH-acidic compound as coinitiator.

BACKGROUND OF THE INVENTION

The restoration of teeth commonly involves a photocurable dental composition containing free radically polymerizable resins. Photocuring of a dental composition involves a photoinitiator system generating free radicals upon exposure to visible light. Conventionally, photosensitizers such as camphorquinone (CQ) optionally in combination with a tertiary aromatic amine are frequently used as photoinitiator systems.

However, the presence of amines in (meth)acrylate containing compositions can cause yellowing in the resulting photocured composition. Another disadvantage of the tertiary aromatic amine is their discoloration tendency and their sensitivity to strong acidic media. Furthermore, aromatic tertiary amines react with oxygen radicals. Thus, while beneficial on the one hand that its use avoids a sticky surface, on the other hand more aromatic amine is needed for initiation than the stoichiometric requirement with the respective photosensitizer such as CQ. Tertiary amines for use as coinitiators in dental compositions may leach out of the cured composition which may give rise to toxicological concern. Especially, the toxicological concerns about tertiary aromatic amines requires the development of new coinitiators for photosensitizers such as CQ in dental materials.

OBJECTIVE OF THE PRESENT INVENTION

In view of the prior art, it was thus an object of the present invention to provide a new dental composition comprising an initiator system, which shall not exhibit the aforementioned shortcomings of the known prior art dental compositions.

In particular, it was an object of the present invention to provide a dental composition comprising an initiator system, which shall be at least substantially free, preferably completely free, of amines, especially of tertiary amines, more especially of tertiary aromatic amines.

What is needed therefore is a way to provide new coinitiators for common photosensitizers, such as camphorquinone, in dental compositions, wherein the coinitiators are free of amines.

Furthermore, it was an object of the present invention to provide a dental composition comprising a radical initiator system containing a combination of a photosensitizer and at least one coinitiator being a CH-acidic compound, wherein such an inventive dental composition can reduce, or ideally avoid or eliminate, the leaching problems and the toxicological concerns of the commonly uses coinitiators based on tertiary aromatic amines, while improving the required biocompatibility simultaneously.

SUMMARY OF THE INVENTION

These objects and also further objects which are not stated explicitly but are immediately derivable or discernible from the connections discussed herein by way of introduction are achieved by a dental composition having all features of claim 1. Appropriate modifications of the dental composition are protected in dependent claims 2 to 15.

The present invention accordingly provides a dental composition comprising
  a) at least one polymerizable monomer having at least one ethylenically unsaturated group;
  characterized in that
  the dental composition further comprises
  b) a radical initiator system comprising
    i. a photosensitizer having an absorption maximum ranging from 400 nm to 800 nm; and
    ii. at least one CH-acidic compound as coinitiator.

It is thus possible in an unforeseeable manner to provide a new dental composition comprising an initiator system, which does not exhibit the aforementioned shortcomings of the known prior art dental compositions.

In particular, the present invention provides a dental composition comprising a radical initiator system, which is at least substantially free, preferably completely free, of amines, especially of tertiary amines, more especially of tertiary aromatic amines.

Thereby, the present invention provides new coinitiators for common photosensitizers, such as camphorquinone, in dental compositions, wherein the coinitiators are free of amines.

Furthermore, a dental composition is provided, which comprises a radical initiator system containing a combination of a photosensitizer and at least one coinitiator being a CH-acidic compound, wherein such an inventive dental composition can reduce, or ideally avoid or eliminate, the leaching problems and the toxicological concerns of the commonly uses coinitiators based on tertiary aromatic amines, while improving the required biocompatibility simultaneously.

The dental composition comprising at least one CH-acidic compound as coinitiator provides improved polymerization efficiency including a good conversion without posing leaching problems of aromatic amines. Such a coinitiator being a CH-acidic compound of the present invention is stable to strong acidic media and thereby suitable for dental application such as adhesives and self-etching preparations. Such coinitiators of the present invention when being incorporated into such a dental composition have low tendency towards discoloration while exhibiting good storage stability at the same time.

The at least one coinitiator being a CH-acidic compound acts by initiating polymerization of one or more polymerizable monomers having at least one ethylenically unsaturated groups. The coinitiators of the present invention provide biocompatibility with reduced release of components when incorporated into such dental compositions.

BRIEF DESCRIPTION OF THE FIGURES

For a more complete understanding of the present invention, reference is made to the following Detailed Description of the Invention considered in conjunction with the accompanying figures, in which.

DETAILED DESCRIPTION OF THE INVENTION

The term "alkyl", unless otherwise specified, refers to a monoradical branched or unbranched saturated hydrocarbon chain having from 1 to 18 carbon atoms. This term can be exemplified by groups such as methyl, ethyl, n-propyl, iso-propyl, n-butyl, iso-butyl, sec-butyl, t-butyl, n-pentyl, isopentyl, neopentyl, n-hexyl, n-decyl, dodecyl, tetradecyl, and the like.

The term "alkoxy group", unless otherwise specified refers to a monoradical branched or unbranched saturated hydrocarbon chain having from 1 to 18 carbon atoms, wherein at least one carbon atom of such an alkoxy group is substituted by one oxygen atom. Such an alkoxy group is attached by said at least one oxygen atom to a carbon atom of a chemical compound. This term can be exemplified by groups such as methoxy, ethoxy, and the like. That means the term "alkoxy group" is defined in the context of the present invention as any chemist would understand it based on common chemical knowledge.

The term "alkylene", unless otherwise specified refers to a linear saturated divalent hydrocarbon radical of one to four carbon atoms or a branched saturated divalent hydrocarbon radical of three to four carbon atoms, e.g., methylene, ethylene, 2,2-dimethylethylene, propylene, 2-methylpropylene, butylene and the like, preferably methylene, ethylene, or propylene.

The term "aryl" refers to C6-C10-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those "aryl" groups having heteroatoms in the ring structure may also be referred to as "heteroaryl" or "heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, and combinations thereof.

The term "cycloalkyl" refers to monocyclic or polycyclic cycloalkyl radical. Examples of monocyclic acycloakyl include cyclopropyl, cyclobutyl, cyclopentyl, cyclohexyl, cycloheptyl, and cyclooctyl. Examples of polycyclic cycloalkyl radical include, for example admantyl, norbornyl, decalinyl, 7,7-dimethyl-bicyclo[2.2.1]heptanyl, tricyclo [5.2.1.02,6]decyl and the like.

The term "(meth)acrylate" in the context of the present disclosure is meant to refer to the acrylate as well as to the corresponding methacrylate.

The term "(meth(acrylamide" in the context of the present disclosure is meant to include acrylamide and methacrylamide.

The term "polymerizable monomer" in the context of the present disclosure means any monomer capable of radical polymerization. The polymerizable monomer includes at least one ethylenically unsaturated groups. The at least one ethylenically unsaturated groups include vinyl, allyl, acryl, methacryl, and styryl.

The term "a polymerizable monomer having at least one ethylenically unsaturated group" and "ethylenically unsaturated monomers" may be used interchangeably.

The term "radical initiator system" in the context of the present disclosure means any system comprising a sensitizer and at least one coinitiator forming free radicals when activate by thermal or light and/or ambient redox conditions, whereby polymerization of polymerizable monomer is initiated.

The term "coinitiator" in the context of the present disclosure means a compound that does not essentially absorb when exposed with UV radiation or visible light but forms free radicals together with the sensitizers used according to the present disclosure.

The term "sensitizer" in the context of the present disclosure which can absorb radiation of a wavelength in the range of 400 to 800 nm, when it is exposed but which cannot by itself, i.e. without the addition of coinitiators, form free radicals. Sensitizers used in the present disclosure have to be capable of interacting with the coinitiators used in the present disclosure.

The present disclosure relates to a dental composition. The dental composition is selected from a dental adhesive, a dental composite, a root canal filling composition, a dental sealant and a dental cement.

The dental composition of the present disclosure comprises one or more polymerizable monomers having at least one ethylenically unsaturated group.

Polymerizable monomers may be acrylates, methacrylates, ethylenically unsaturated compounds, carboxyl group-containing unsaturated monomers, C2-8 hydroxyl alkyl esters of (meth)acrylic acid, C1-24 alkyl esters or cycloalkyl esters of (meth)acrylic acid, C2-18 alkoxy-alkyl esters of (meth)acrylic acid, olefins or diene compounds, monoesters/ diesters, monoethers, adducts, vinyl monomer, styryl monomer, TPH resin, SDR Resin, PBA resins and/or BPA-free resins.

A Radical Initiator System

The dental composition of the present disclosure includes a radical initiator system. The radical initiator system may include a photoinitiator. Suitable photoinitiators may be in the form of a binary or tertiary system. A binary system may include a photosensitizer and a CH-acidic compound as coinitiator. A tertiary system may further include additionally an iodonium, sulfonium or phosphonium salt.

In the context of the present invention, the expression "CH-acidic compound" refers to an "α-CH-acidic compound". This definition at the latest is clear understandable (s.a. general textbooks of organic chemistry like "Organikum").

Such CH-acidic compounds can comprise a further functionality, such as at least one ethylenically unsaturated group, which allows taking part in the polymerization process as the at least one polymerizable monomer.

This can be an additional advantage of making use such specific coinitiators, which are not only suitable to replace toxic amine based coinitiators, but also offers the possibility of being incorporated into the growing polymerization chain.

In one embodiment, the at least one CH-acidic compound is a compound according to the following formula (I):

Formula (I)

wherein
- $R_7$, $R_{10}$=a $C_1$-$C_8$ alkoxy, a $C_1$-$C_8$ alkyl, a hydroxy, a thiol, an amine, or a —OCH$_2$CH$_2$OC(O)C(CH$_3$)CH$_2$ moiety; preferably a methoxy, an ethoxy, a hydroxy, an amine, a methyl, or a —OCH$_2$CH$_2$OC(O)C(CH$_3$)CH$_2$ moiety; and
- $R_8$, $R_9$=a hydrogen, a $C_1$-$C_8$ alkyl, or an acetyl moiety; preferably a hydrogen, a methyl, or an acetyl moiety; with the proviso that at least $R_8$ or $R_9$ is a hydrogen moiety.

In a preferred embodiment thereof, the at least one CH-acidic compound is a compound according to one of the following formulas (Ia) and (Ib):

Formula (Ia)

wherein $R_8$, $R_9$=a hydrogen, a $C_1$-$C_8$ alkyl, or an acetyl moiety; preferably a hydrogen, a methyl, or an acetyl moiety; with the proviso that at least $R_8$ or $R_9$ is a hydrogen moiety; and
$R_{11}$, $R_{12}$=a hydrogen, a $C_1$-$C_8$ alkyl, or a —CH$_2$CH$_2$OC(O)C(CH$_3$)CH$_2$ moiety; preferably a hydrogen, a methyl, an ethyl or a —CH$_2$CH$_2$OC(O)C(CH$_3$)CH$_2$ moiety;

Formula (Ib)

wherein
- $R_7$=a $C_1$-$C_8$ alkoxy, a $C_1$-$C_8$ alkyl, a hydroxy, a thiol, an amine, or a —OCH$_2$CH$_2$OC(O)C(CH$_3$)CH$_2$ moiety; preferably a methoxy, an ethoxy, a hydroxy, an amine, a methyl, or a —OCH$_2$CH$_2$OC(O)C(CH$_3$)CH$_2$ moiety;
- $R_8$, $R_9$=a hydrogen, a $C_1$-$C_8$ alkyl, or an acetyl moiety; preferably a hydrogen, a methyl, or an acetyl moiety; with the proviso that at least $R_8$ or $R_9$ is a hydrogen moiety; and
- $R_{12}$=a hydrogen, a $C_1$-$C_8$ alkyl, or a —CH$_2$CH$_2$OC(O)C(CH$_3$)CH$_2$ moiety; preferably a hydrogen, a methyl, an ethyl or a —CH$_2$CH$_2$OC(O)C(CH$_3$)CH$_2$ moiety;
- preferably wherein the at least one CH-acidic compound is ethyl 2-methylacetoacetate (HD-3), ethyl diacetoacetate (HD-5), or 2-(methacryloyloxy) ethyl acetoacetate (HD-10).

In one alternative embodiment, the at least one CH-acidic compound is a compound according to the following formula (II):

Formula (II)

wherein
- $R_{13}$=a hydrogen, a $C_1$-$C_8$ alkyl, a carboxylic acid, an acetyl, or a —CH$_2$OC(O)C(CH$_3$)CH$_2$ moiety; wherein the $C_1$-$C_8$ alkyl moiety can be substituted by at least a nitrile group, a hydroxy group, or a carboxylic acid group;
- preferably a methyl, a —CH$_2$OH, a —COOH, a —CH$_2$COOH, a —CH$_2$CN, an acetyl, or a —CH$_2$OC(O)C(CH$_3$)CH$_2$ moiety.

In a preferred embodiment thereof, the at least one CH-acidic compound is a compound according to one of the following formulas (IIa) and (IIb):

Formula (IIa)

wherein
$R_{14}$=a hydrogen, a $C_1$-$C_8$ alkyl, or a hydroxy moiety; preferably a methyl or a hydroxy moiety.

Formula (IIb)

wherein
R₁₅=a hydrogen, a hydroxy, a carboxylic acid, a nitrile, or a —OC(O)C(CH₃)CH₂ moiety.

In another alternative embodiment, the at least one CH-acidic compound is a compound according to the following formula (III):

Formula (III)

wherein
R₁₆=a hydrogen, a C₁-C₁₈ alkyl, or a C₁-C₁₈ cycloalkyl moiety; wherein in the C₁-C₈ alkyl or cycloalkyl moiety at least one carbon atom can be substituted by nitrogen; and wherein the C₁-C₈ alkyl or cycloalkyl moiety can be substituted by at least a double bonded oxygen atom, an aromatic and/or an heteroaromatic group;
preferably wherein the at least one CH-acidic compound is N-(diphenyl-methylene) glycine ethyl ester (HD-1), ethyl 2-oxocyclopentanecarboxylate (HD-2), or ethyl 2-ethyl-2-methylacetoacetate (HD-4).

In another alternative embodiment, the at least one CH-acidic compound is a compound according to the following formula (IV):

Formula (IV)

wherein
R₁₇, R₁₈=a hydrogen or a C₁-C₈ alkyl moiety;
preferably wherein the at least one CH-acidic compound is dimethyl 1,4-cyclohexanedione-2,5-dicarboxylate (HD-6).

In another alternative embodiment, the at least one CH-acidic compound is a compound according to the following formula (V):

Formula (V)

wherein
R₁₉, R₂₀=a hydrogen or a C₁-C₈ alkyl moiety;
preferably wherein the at least one CH-acidic compound is dehydroacetic acid (HD-7).

In another alternative embodiment, the at least one CH-acidic compound is a compound according to the following formula (VI):

Formula (VI)

wherein
R₁, R₂, R₃, R₄, R₅, R₆=a hydrogen, a C₁-C₈ alkyl, a carboxylic acid, an acetyl, or a —OC(O)CHCH₂ moiety; with the proviso that at least R₁, R₂, R₅, or R₆, preferably R₅ or R₆, is a hydrogen moiety;
preferably wherein the at least one CH-acidic compound is a compound according to the following formula (VIa):

Formula (VIa)

wherein
R₃, R₄, R₆=a hydrogen, a C₁-C₈ alkyl, a carboxylic acid, an acetyl, or a —OC(O)CHCH₂ moiety;
and more preferably wherein the at least one CH-acidic compound is α-acetylbutyrolactone (HD-8) or (R)-α-acryloyloxy-β,β-dimethyl-γ-butyrolactone (HD-9).

In formula (VIa), R₁, R₂, and R₅ are a hydrogen moiety, respectively.

Conclusively, according to one embodiment of the present invention, the at least one CH-acidic compound is a compound according to one of the above-defined formulas (I), (Ia), (Ib), (II), (IIa), (IIb), (III), (IV), (V), (VI), and (VIa), If more than one CH-acidic compound is comprised by the inventive radical initiator system, all comprised CH-acidic compounds can be compounds according to the same formula (I), (Ia), (Ib), (II), (IIa), (IIb), (III), (IV), (V), (VI), or (VIa).

Alternatively, if more than one CH-acidic compound is comprised by the inventive radical initiator system, each of the comprised CH-acidic compounds can be a compound according to a formula (I), (Ia), (Ib), (II), (IIa), (IIb), (III), (IV), (V), (VI), or (VIa), wherein two CH-acidic compounds are never being compounds according to the same formula (I), (Ia), (Ib), (II), (IIa), (IIb), (III), (IV), (V), (VI), or (VIa).

As a further alternative, if more than one CH-acidic compound is comprised by the inventive radical initiator system, at least two of the comprised CH-acidic compounds can be a compound according to the same formula (I), (Ia), (Ib), (II), (IIa), (IIb), (III), (IV), (V), (VI), or (VIa).

In one embodiment, the dental composition further comprises an additive selected from iodonium salts, phosphonium salts, and sulfonium salts; preferably wherein said additive is an iodonium salt.

In one preferred embodiment thereof, the additive is present in an amount of from 0.01 to 5 percent by weight based on the total weight of the dental composition.

Such an iodonium compound can comprise the following Formula (C):

Formula (C)

wherein $R_{21}$ and $R_{22}$ are independent from each other, represent an organic moiety, and $A^-$ is an anion.

In embodiments, iodonium compounds include diphenyliodonium (DPI) hexafluorophosphate, di(4-methylphenyl) iodonium (Me2-DPI) hexafluorophosphate, di-(4-t-butylphenyl)-iodonium hexafluorophosphate, diaryliodonium hexafluoroantimonate, (4-methylphenyl)[4-(2-methylpropyl)phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl) phenyliodonium hexafluoroantimonate, and 4-isopropyl-4'-methyldiphenyliodonium borate.

According to a further embodiments, the iodonium compound is di-(4-t-butylphenyl)-iodonium hexafluorophosphate, di(4-methylphenyl)iodonium (Me2-DPI) hexafluorophosphate, or Bis(4-tert-butylphenyl)iodonium p-toluenesulfonate.

According to yet further embodiments, the photo initiator may include a sulfonium compound of the following Formula (D):

$R_{23}R_{24}R_{25}S^+A^-$      Formula (D)

wherein $R_{23}$, $R_{24}$ and $R_{25}$ are independent from each other, represent an organic moiety or wherein any two of $R_{23}$, $R_{24}$ and $R_{25}$ form a cyclic structure together with the sulfur atom to which they are bound, and $A^-$ is an anion.

The triaryl sulfonium salt may be S-(phenyl)thianthrenium hexafluorophosphate:

PF$_6$

According to a further embodiment, the photo initiator may include a phosphonium compound of the following Formula (E):

$R_{26}R_{27}R_{28}R_{29}P^+A^-$      Formula (E)

wherein $R_{26}$, $R_{27}$, $R_{28}$ and $R_{29}$ are independent from each other, represent an organic moiety, and $A^-$ is an anion.

The phosphonium salts of Formula (E) may be tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

Other suitable photoinitiators for polymerizing free radically photopolymerizable compositions may include the class of phosphine oxides that typically have a functional wavelength range of about 380 nm to about 1200 nm. Further suitable phosphine oxide free radical initiators with a functional wavelength range of about 380 nm to about 450 nm are acyl and bisacyl phosphine oxides.

In one embodiment, the photosensitizer is a 1, 2-diketone compound, preferably wherein the photosensitizer is present in an amount of from 0.01 to 5 percent by weight based on the total weight of the dental composition.

The alpha-diketone sensitizer compound may be selected from camphorquinone, 1,2-diphenylethane-1,2-dione (benzil), 1,2-cyclohexanedione, 2,3-pentanedione, 2,3-hexanedione, 3,4-hexanedione, 2,3-heptanedione, 3,4-heptanedione glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione; 3,3,18,18-tetramethyl-1,2-cyclooctadecanedione; dipivaloyl; furil, hydroxybenzil, 2,3-butanedione, 2,3-octanedione, 4,5-octanedione, and 1-phenyl-1,2-propanedione.

In one embodiment, the radical initiator system is present in an amount of from 0.1 to 10 percent by weight based on the total weight of the dental composition.

In one embodiment, the at least one CH-acidic compound is present in an amount of from 0.01 to 5 percent by weight based on the total weight of the dental composition.

In one embodiment, the dental composition comprises a radical initiator system, which is at least substantially free, preferably completely free, of amines, especially of tertiary amines, more especially of tertiary aromatic amines.

The present invention thus addresses the problem of providing an inventive dental composition comprising an amended initiator system.

The following non-limiting examples are provided to illustrate an embodiment of the present invention and to facilitate understanding of the invention but are not intended to limit the scope of the invention, which is defined by the claims appended hereto.

Compounds used in inventive and comparative experiments are given in the following:

Camphorquinone (CQ)

Ethyl 4-(dimethylamino)benzoate (DMABE)

Bis-(4-t-butylphenyl)-iodonium hexaflourophosphate (SC938)

Bis-(4-t-butylphenyl)iodonium p-toluenesulfonate

N-(Diphenylmethylene)glycine ehtyl ester
HD-1

Ethyl 2-oxocyclopentanecarboxylate
HD-2

Ethyl 2-methylacetoacetate
HD-3

Ethyl 2-ethyl-methylacetoacetate
HD-4

Ethyldiacetoacetate
HD-5

Dimethyl 1,4-cyclohexanedione-2,5-dicarboxylate
HD-6

Dehydroacetic acid
HD-7

α-acetylbutyrolactone
HD-8

(R-α-acryloyloxy-β,β-dimethyl-γ-butyrolactone
HD-9

2-(methacryloyloxy)ethylacetoacetate
HD-10

Herein, "SC938" refers to "speedcure 938".

Example 1

Use of (R)-α-acyloyl-γ-butyrolactone (HD-8) as Coinitiator for Polymerization of TPH3 Resin (a Methacrylate Resin)

Figure 1:
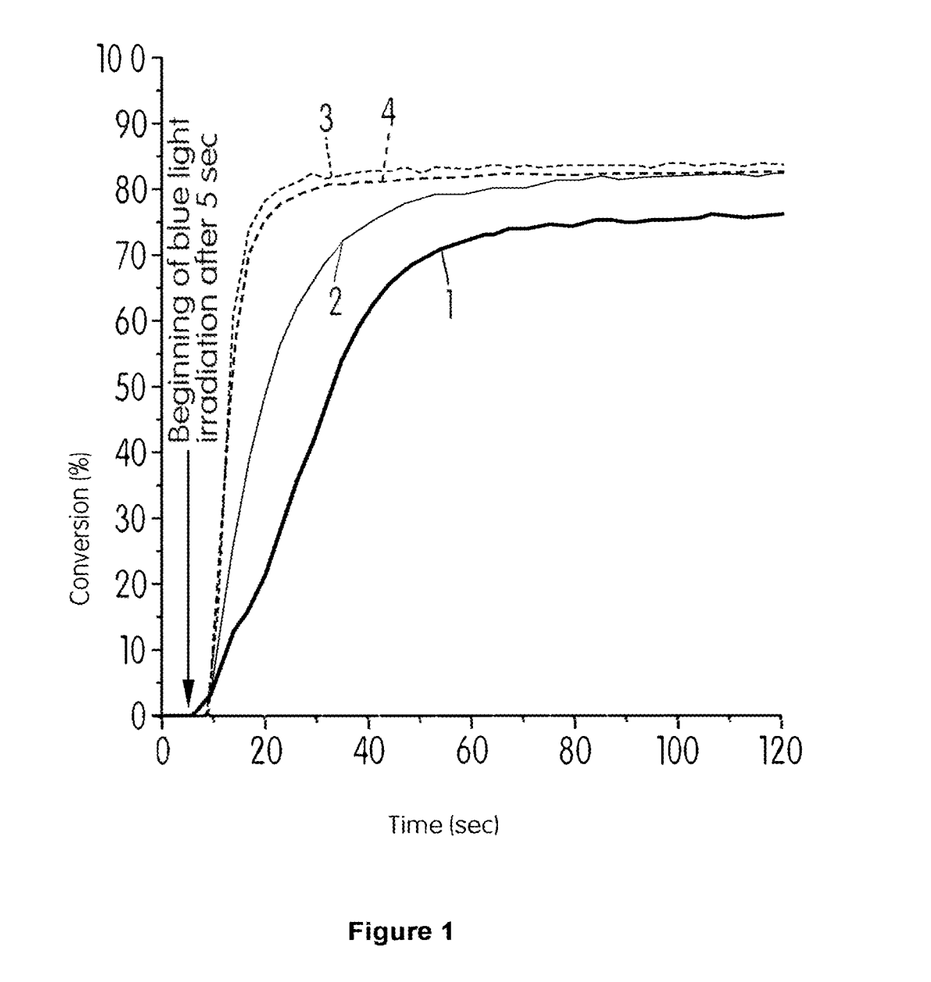
FIG. 1 depicts photopolymerization profiles of methacrylate functions (TPH3) in presence of (1) CQ (0.5% wt) or (2) CQ/lactone (HD-8) (0.5/3% w/w) or (3) CQ/lactone (HD-8)/Speedcure 938 (0.5/3/1% w/w) or (4) CQ/DMABE (0.5/1% w/w) under exposure to Smartlite Focus (300 mW·cm-2); sample thickness 1.4 mm: under air.

Photopolymerization profiles of methacrylate functions (TPH3) in presence of (1) CQ (0.5% wt) or (2) CQ/lactone (HD-8) (0.5/3% w/w) or (4) CQ/DMABE (0.5/1% w/w) or (3) CQ/lactone (HD-8)/Speedcure 938 (0.5/3/1% w/w) under exposure to Smartlite Focus (300 mW·cm$^{-2}$); sample thickness 1.4 mm; under air. (as shown in FIG. 1). It was observed that there is good reactivity of CQ/lactone (HD-8)/speedcure 938 in TPH3. It is similar to CQ/DMABE, but amine free system.

Herein, it is clearly demonstrated that the use of a CH-acidic coinitiator in combination with CQ is better performing than CQ alone. Furthermore, it is shown that CQ with the CH-acidic coinitiator and an iodonium compound in a ternary system is even still much better performing than the binary system of CQ with the respective identical CH-acidic coinitiator. The comparative example of CQ with the tertiary amine DMABE shows a similar performance than the inventive ternary system example. This proves that the present invention has successfully provided a suitable dental composition comprising an initiator system, which can deliver the same performance than the environmentally toxic commonly used initiator system of CQ in combination with a tertiary amine as coinitiator.

Example 2

Use of (R)-α-acyloyl-γ-butyrolactone (HD-8) as Coinitiator for Polymerization of Prime & Bond Active Resin (a Methacrylate Resin)

Figure 2:
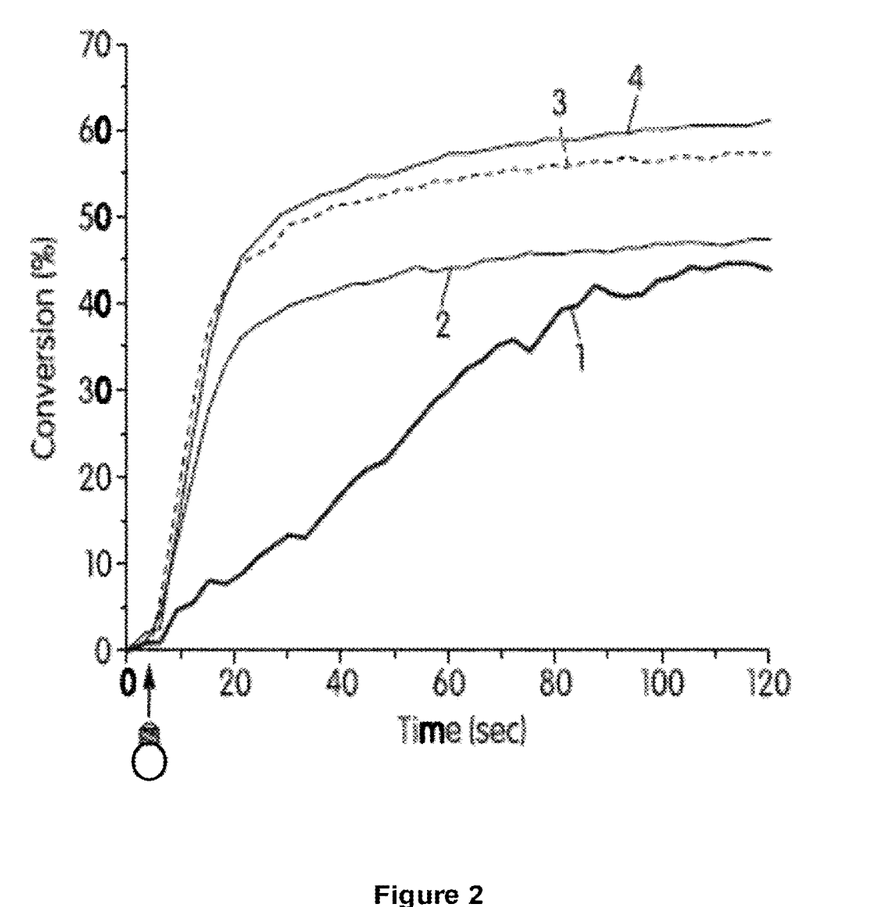
FIG. 2 depicts photopolymerization profiles of C=C double bonds (PrimeBond Active) in presence of (1) CQ (1.5% w/w) or (2) CQ/Speedcure 938 (1.5/0.75% w/w) or (3) CQ/acetylbutyrolactone (HD-8)/iodonium sulfonate (1.5/1.2/0.75% w/w) or (4) CQ/acetylbutyrolactone (HD-8)/ Speedcure938 (1.5/1.2/0.75% w/w) or under exposure to SmartLite Focus (300 mW·cm-2); sample thickness 17 μm; under air.

Photopolymerization profiles of C=C double bonds (PrimeBond Active) in presence of (1) CQ (1.5% w/w) or (2) CQ/Speedcure 938 (1.5/0.75% w/w) or (3) CQ/acetylbutyrolactone (HD-8)/Bis(4-t-butylphenyl)iodonium p-toluenesulfonate (1.5/1.2/0.75% w/w) or (4) CQ/acetyl-butyrolactone (HD-8)/Speedcure938 (1.5/1.2/0.75% w/w) or under exposure to SmartLite Focus (300 mW·cm-2); sample thickness 17 µm; under air (FIG. 2).

It was observed that there is good reactivity of CQ/lactone (HD-8)/speedcure 938 and CQ/lactone/iodoinium sulfonate in PBA. It is an amine free system. Slight tacky polymers were obtained.

Herein, it is clearly demonstrated that the performance of a ternary inventive initiator system of CQ in combination with a CH-acidic compound and an iodonium compound is better than either CQ alone or the combination of CQ with an iodonium ion. This proves that the suitable performance shown in FIG. 1 is depending on the CH-acidic compound. A combination of an iodonium compound with CQ is not superior and does not represent an alternative. However, if additionally used with CQ and a CH-acidic compound, the use of such an iodonium compound has shown to be senseful in order to further improve the performance of the binary system of CQ and the respective CH-acidic compound.

Example 3

Systematic Investigation of a Plurality of CH-Acidic Compounds in Combination with CQ Plus Comparison to CQ Alone and in Combination with a Tertiary amine (DMABE)

Figure 3:
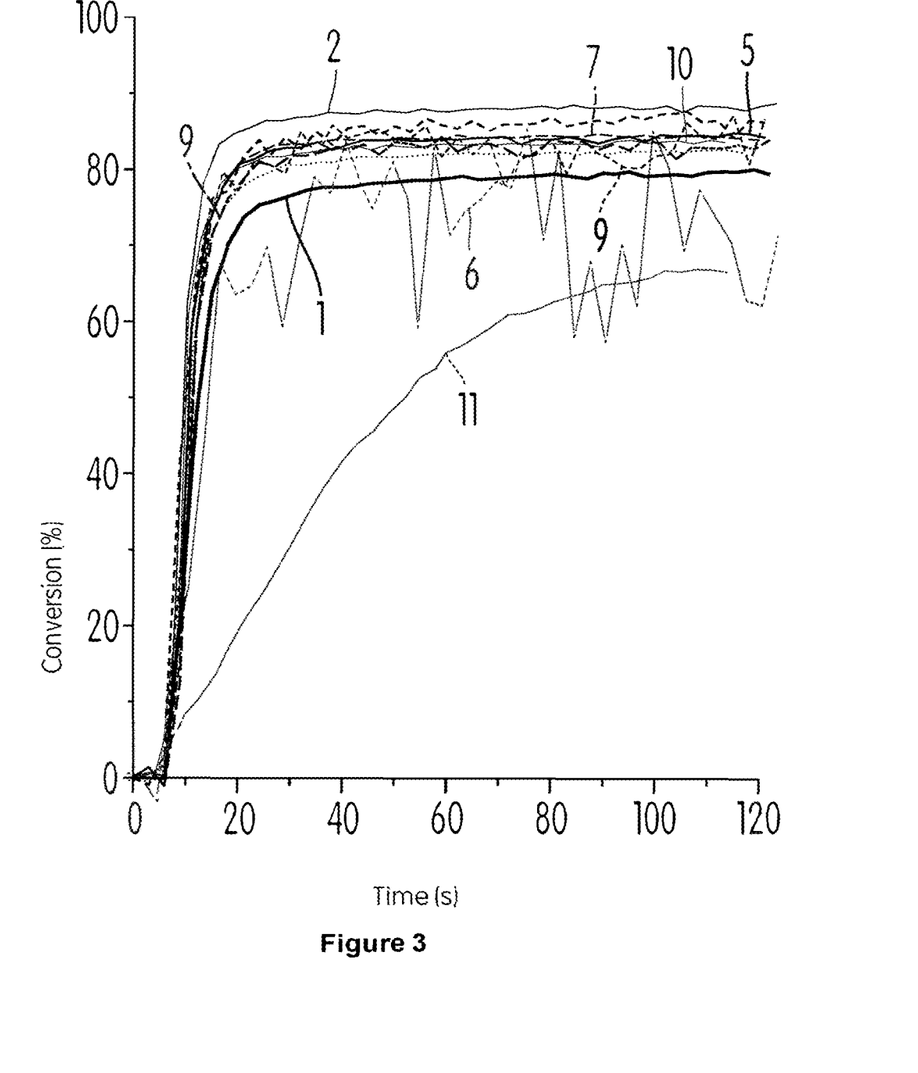
FIG. 3 depicts photopolymerization profiles of methacrylate functions (TPH3) in presence of camphorquinone as photoinitiator (under air; thickness=1.4 mm; SmartLite Focus 300 mW·cm-2): (1) CQ/HD-1/SC938 (0.5/3/1% w/w) (2) CQ/HD-2/SC938 (0.5/3/1% w/w) (3) CQ/HD-3/SC938 (0.5/3/1% w/w) (4) CQ/HD-4/SC938 (0.5/3/1% w/w) (5) CQ/HD-5/SC938 (0.5/3/1% w/w) (6) CQ/HD-6/SC938 (0.5/3/1% w/w) (7) CQ/HD-7/SC938 (0.5/3/1% w/w) (8) CQ/HD-8/SC938 (0.5/3/1% w/w) (9) CQ/HD-10/SC938 (0.5/3/1% w/w) (10) CQ/DMABE (0.5/0.5% w/w) (11) CQ (0.5% w/w). The irradiation starts for t=5 s.

Photopolymerization profiles of methacrylate functions (TPH3) in presence of camphorquinone as photoinitiator (under air; thickness=1.4 mm; SmartLite Focus 300 mW·cm$^{-2}$): (1) CQ/HD-1/SC938 (0.5/3/1% w/w) (2) CQ/HD-2/SC938 (0.5/3/1% w/w) (3) CQ/HD-3/SC938 (0.5/3/1% w/w) (4) CQ/HD-4/SC938 (0.5/3/1% w/w) (5) CQ/HD-5/SC938 (0.5/3/1% w/w) (6) CQ/HD-6/SC938 (0.5/3/1% w/w) (7) CQ/HD-7/SC938 (0.5/3/1% w/w) (8) CQ/HD-8/SC938 (0.5/3/1% w/w) (9) CQ/HD-10/SC938 (0.5/3/1% w/w) (10) CQ/DMABE (0.5/0.5% w/w) (11) CQ (0.5% w/w). The irradiation starts for t=5 s (as depicted in FIG. 3).

New CH-acidic compounds (HD-1 to HD-10) were used as efficient co-initiators in combination with camphorquinone (CQ) for the free radical polymerization of methacrylates under air and under exposure to a blue dental LED (SmartLite Focus-Dentsply Sirona). Remarkably, they can be used in combination with CQ and an iodonium salt and these amine-free systems present excellent polymerization performances, even in comparison to the current comparative reference systems CQ/DMABE and CQ alone. For example, the polymerizations of TPH3 resin (a methacrylate resin) in presence of CQ/CH-acidic compound/SC938 using 9 different CH-acidic compounds as coinitiator in the respectively investigated photoinitiating system are shown in FIG. 3.

Herein, it is again proven that the performance of a ternary inventive initiator system of CQ in combination with a CH-acidic compound and an iodonium compound is better than either CQ alone or at least similar to a combination of CQ with a commonly used tertiary amine (DMABE) as coinitiator.

Example 4

Figure 4:
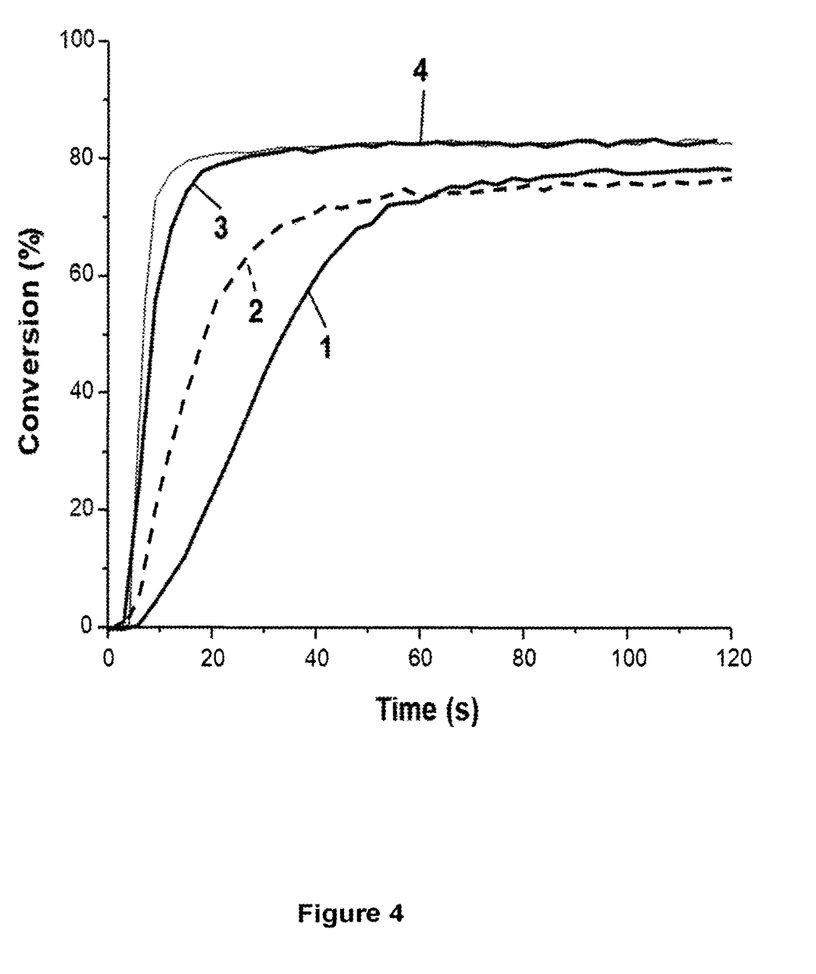
FIG. 4 represents photopolymerization profiles of methacrylate functions (TPH3) in presence of camphorquinone as photoinitiator (under air; thickness=1.4 mm; SmartLite Focus 300 mW·cm-2): (1) CQ/TPH3 (0.5/100% w/w) (2) CQ/HD-9/TPH3 (0.5/5/95% w/w) (3) CQ/HD-9/SC938/ TPH3 (0.5/5/1/100% w/w) (4) CQ/DMABE/TPH3 (0.5/0.6/ 100% w/w) (5) CQ/DMABE/HD-9/TPH3 (0.5/0.6/5/95% w/w). The irradiation starts for t=5 s.

Use of (R)-α-acryloyloxy-β,β-dimethyl-γ-butyrolactone (HD-9) as Coinitiator (R)-α-acryloyloxy-β,β-dimethyl-γ-butyrolactone (HD-9) was proposed as a new coinitiator in combination with camphorquinone. For example, the polymerizations of TPH3 resin in presence of CQ/HD-9, CQ/HD-9/SC938 and CQ/DMABE/HD-9 as photoinitiating systems are shown in FIG. 4. The amine-free system CQ/HD-9/SC938 presents excellent polymerization performances similar to the reference comparative system CQ/DMABE.

Photopolymerization profiles of methacrylate functions (TPH3) in presence of camphorquinone as photoinitiator (under air; thickness=1.4 mm; SmartLite Focus 300 mW·cm$^{-2}$): (1) CQ/TPH3 (0.5/100% w/w) (2) CQ/HD-9/TPH3 (0.5/5/95% w/w) (3) CQ/HD-9/SC938/TPH3 (0.5/5/1/100% w/w) (4) CQ/DMABE/TPH3 (0.5/0.6/100% w/w). The irradiation starts for t=5 s. (as depicted in FIG. 4).

While the principles of the invention have been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims. The scope of the invention is limited only by the scope of the appended claims.

The invention claimed is:

1. Dental composition comprising
   a) at least one polymerizable monomer having at least one ethylenically unsaturated group;
   characterized in that
   the dental composition further comprises
   b) a radical initiator system comprising
      i. a photosensitizer having an absorption maximum ranging from 400 nm to 800 nm; and
      ii. at least one CH-acidic compound as coinitiator and
   c) an additive selected from iodonium salts, phosphonium salts, and sulfonium salts, wherein the radical initiator system is substantially free of an amine.

2. Dental composition according to claim 1 characterized in that the at least one CH-acidic compound is a compound according to the following formula (I):

Formula (I)

wherein
$R_7$, $R_{10}$=a $C_1$-$C_8$ alkoxy, a $C_1$-$C_8$ alkyl, a hydroxy, a thiol, an amine, or a —OCH$_2$CH$_2$OC(O)C(CH$_3$)CH$_2$ moiety; and
$R_8$, $R_9$=a hydrogen, a $C_1$-$C_8$ alkyl, or an acetyl moiety; with the proviso that at least $R_8$ or $R_9$ is a hydrogen moiety.

3. Dental composition according to claim 2 characterized in that the at least one CH-acidic compound is a compound according to one of the following formulas (Ia) and (Ib):

Formula (Ia)

wherein
R$_8$, R$_9$=a hydrogen, a C$_1$-C$_8$ alkyl, or an acetyl moiety; with the proviso that at least R$_8$ or R$_9$ is a hydrogen moiety; and
R$_{11}$, R$_{12}$=a hydrogen, a C$_1$-C$_8$ alkyl, or a —CH$_2$CH$_2$OC(O)C(CH$_3$)CH$_2$ moiety;

Formula (Ib)

wherein
R$_7$=a C$_1$-C$_8$ alkoxy, a C$_1$-C$_8$ alkyl, a hydroxy, a thiol, an amine, or a —OCH$_2$CH$_2$OC(O)C(CH$_3$)CH$_2$ moiety;
R$_8$, R$_9$=a hydrogen, a C$_1$-C$_8$ alkyl, or an acetyl moiety; with the proviso that at least R$_8$ or R$_9$ is a hydrogen moiety; and
R$_{12}$=a hydrogen, a C$_1$-C$_8$ alkyl, or a —CH$_2$CH$_2$OC(O)C(CH$_3$)CH$_2$ moiety.

4. Dental composition according to claim 1 characterized in that the at least one CH-acidic compound is a compound according to the following formula (II):

Formula (II)

wherein
R$_{13}$=a hydrogen, a C$_1$-C$_8$ alkyl, a carboxylic acid, an acetyl, or a —CH$_2$OC(O)C(CH$_3$)CH$_2$ moiety; wherein the C$_1$-C$_8$ alkyl moiety can be substituted by at least a nitrile group, a hydroxy group, or a carboxylic acid group.

5. Dental composition according to claim 4 characterized in that the at least one CH-acidic compound is a compound according to one of the following formulas (IIa) and (IIb):

Formula (IIa)

wherein
R$_{14}$=a hydrogen, a C$_1$-C$_8$ alkyl, or a hydroxy moiety

Formula (IIb)

wherein
R$_{15}$=a hydrogen, a hydroxy, a carboxylic acid, a nitrile, or a —OCH$_2$CH$_2$OC(O)C(CH$_3$)CH$_2$ moiety.

6. Dental composition according to claim 1 characterized in that the at least one CH-acidic compound is a compound according to the following formula (III):

Formula (III)

wherein
R$_{16}$=a hydrogen, a C$_1$-C$_{18}$ alkyl, or a C$_1$-C$_{18}$ cycloalkyl moiety; wherein in the C$_1$-C$_8$ alkyl or cycloalkyl moiety at least one carbon atom can be substituted by nitrogen; and wherein the C$_1$-C$_8$ alkyl or cycloalkyl moiety can be substituted by at least a double bonded oxygen atom, an aromatic and/or an heteroaromatic group.

7. Dental composition according to claim 1 characterized in that the at least one CH-acidic compound is a compound according to the following formula (IV):

(IV)

wherein
R$_{17}$, R$_{18}$=a hydrogen or a C$_1$-C$_8$ alkyl moiety.

8. Dental composition according to claim 1 characterized in that the at least one CH-acidic compound is a compound according to the following formula (V):

Formula (V)

wherein
R$_{19}$, R$_{20}$=a hydrogen or a C$_1$-C$_8$ alkyl moiety.

9. Dental composition according to claim 1 characterized in that the at least one CH-acidic compound is a compound according to the following formula (VI):

Formula (VI)

wherein
R$_1$, R$_2$, R$_3$, R$_4$, R$_8$, R$_6$=a hydrogen, a C$_1$-C$_8$ alkyl, a carboxylic acid, an acetyl, or a —OC(O)CHCH$_2$ moiety; with the proviso that at least R$_1$, R$_2$, R$_5$, or R$_6$ is a hydrogen moiety.

10. Dental composition according to claim 1 characterized in that the additive is present in an amount of from 0.01 to 5 percent by weight based on the total weight of the dental composition.

11. Dental composition according to claim 1 characterized in that the photosensitizer is a 1, 2-diketone compound, and wherein the photosensitizer is present in an amount of from 0.01 to 5 percent by weight based on the total weight of the dental composition.

12. Dental composition according to claim 1 characterized in that the radical initiator system is present in an amount of from 0.1 to 10 percent by weight based on the total weight of the dental composition.

13. Dental composition according to claim 1 characterized in that the at least one CH-acidic compound is present in an amount of from 0.01 to 5 percent by weight based on the total weight of the dental composition.

14. Dental composition according to claim 3, wherein the at least one CH-acidic compound is ethyl 2-methylacetoacetate (HD-3), ethyl diacetoacetate (HD-5), or 2-(methacryloyloxy)ethyl acetoacetate (HD-10).

15. Dental composition according to claim 6, wherein the at least one CH-acidic compound is N-(diphenylmethylene) glycine ethyl ester (HD-1), ethyl 2-oxocyclopentanecarboxylate (HD-2), or ethyl 2-ethyl-2-methylacetoacetate (HD)-4).

16. Dental composition according to claim 7, wherein the at least one CH-acidic compound is dimethyl 1,4-cyclohexanedione-2,5-dicarboxylate (HD-6).

17. Dental composition according to claim 8, wherein the at least one CH-acidic compound is dehydroacetic acid (HD-7).

18. Dental composition according to claim 9, wherein the at least one CH-acidic compound is a compound according to the following formula (VIa):

Formula (VIa)

wherein
$R_3$, $R_4$, $R_6$=a hydrogen, a $C_1$-$C_8$ alkyl, a carboxylic acid, an acetyl, or a —OC(O)CHCH$_2$ moiety.

19. Dental composition according to claim 17, wherein the at least one CH-acidic compound is α-acetylbutyrolactone (HD-8) or (R)-α-acryloyloxy-β,β-dimethyl-γ-butyrolactone (HD-9).

* * * * *

UNITED STATES PATENT AND TRADEMARK OFFICE
CERTIFICATE OF CORRECTION

PATENT NO. : 12,303,574 B2
APPLICATION NO. : 17/638474
DATED : May 20, 2025
INVENTOR(S) : Klee et al.

Page 1 of 1

It is certified that error appears in the above-identified patent and that said Letters Patent is hereby corrected as shown below:

On the Title Page

In item (71), in "Applicants", in Column 1, Line 2, delete "DETRELY" and insert --DETREY-- therefor In item (72), in "Inventors", in Column 1, Line 2, delete "Neukirchen-Vlyun" and insert --Neukirchen-Vluyn-- therefor In item (73), in "Assignee", in Column 1, Line 1, delete "Dentslpy" and insert --Dentsply-- therefor In the Claims In Column 16, Lines 40-47, in Claim 8, delete "  " and insert --  -- therefor In Column 16, Line 64, in Claim 9, delete "R$_8$," and insert --R$_5$,-- therefor In Column 17, Line 26, in Claim 15, delete "(HD)-4)." and insert --(HD-4).-- therefor Signed and Sealed this
Ninth Day of September, 2025

Coke Morgan Stewart
*Acting Director of the United States Patent and Trademark Office*